US008409224B2

(12) United States Patent
Shriver

(10) Patent No.: US 8,409,224 B2
(45) Date of Patent: Apr. 2, 2013

(54) SUTURING GRAFT TUBES TO LUMEN WALLS PERCUTANEOUSLY

(76) Inventor: Edgar L Shriver, Aventura, FL (US)

( * ) Notice: Subject to any disclaimer, the term of this patent is extended or adjusted under 35 U.S.C. 154(b) by 187 days.

(21) Appl. No.: 12/924,746

(22) Filed: Oct. 4, 2010

(65) Prior Publication Data

US 2012/0083808 A1 Apr. 5, 2012

(51) Int. Cl.
*A61B 17/04* (2006.01)

(52) U.S. Cl. ........ 606/144; 606/148; 606/153; 606/228; 623/1.23

(58) Field of Classification Search .................. 606/144, 606/148, 153, 228; 623/1.11, 1.13, 1.23
See application file for complete search history.

(56) References Cited

U.S. PATENT DOCUMENTS 3,334,629 A 8/1967 Cohn
3,494,006 A 2/1970 Brumlik
4,503,569 A 3/1985 Dotter
4,553,543 A * 11/1985 Amarasinghe ................ 606/148
4,733,665 A 3/1988 Palmaz
4,893,623 A 1/1990 Rosenbluth
5,002,563 A 3/1991 Pyka
5,163,955 A 11/1992 Love
5,197,978 A 3/1993 Hess
5,330,503 A * 7/1994 Yoon ............................ 606/223
5,662,700 A 9/1997 Lazarus
5,810,870 A 9/1998 Meyers
5,957,973 A * 9/1999 Quiachon et al. ............ 623/1.23
5,980,539 A * 11/1999 Kontos .......................... 606/148
6,024,747 A * 2/2000 Kontos .......................... 606/144
6,264,684 B1 7/2001 Banas
6,416,522 B1 * 7/2002 Strecker ........................ 606/143
6,454,778 B2 * 9/2002 Kortenbach .................. 606/144
6,652,570 B2 11/2003 Smith
7,081,131 B2 * 7/2006 Thornton ..................... 623/1.24
7,713,215 B2 5/2010 Shriver
7,771,442 B2 8/2010 Shriver
2003/0149447 A1 * 8/2003 Morency et al. .............. 606/228
2003/0158562 A1 * 8/2003 Feigl ............................. 606/148
2003/0163144 A1 * 8/2003 Weadock et al. ............. 606/153
2004/0068276 A1 * 4/2004 Golden et al. ................ 606/153

* cited by examiner

*Primary Examiner* — Corrine M McDermott
*Assistant Examiner* — Alexander Orkin

(57) ABSTRACT

A graft tube is percutaneously placed inside the lumen of a vessel and attached to the lumen wall by loops of suture material. The plurality of short sutures are made in the shape of a loop with a sharp and a blunt end then forced into a plurality of first tunnels located in sections of circular cuffs that are attached to graft tube ends. The short sutures are pushed out the first tunnel by push rods and curve back to their original shape through the adjacent lumen wall and into a plurality of second tunnels where the short sutures are lodged.

14 Claims, 3 Drawing Sheets

SUTURING GRAFT TUBES TO LUMEN WALLS PERCUTANEOUSLY

CROSS-REFERENCE TO RELATED APPLICATIONS

This is a new invention by the inventor of devices disclosed in U.S. Pat. No. 7,771,442 and U.S. Pat. No. 7,713,215, the object of those patents being to connect a first tube to a second intersecting tube and the present object being to connect a first tube to a second tube located concentrically within the first tube. The means described in the prior patents will not accomplish the object of the present application so this application is submitted to accomplish the new objective by similar other means.

FEDERALLY SPONSORED RESEARCH

Not Applicable

SEQUENCE LISTING OR PROGRAM

Not Applicable

BACKGROUND OF THE INVENTION

1. Field of the Invention

The field generally relates to connecting graft tubes to vessels after entering the vasculature through a skin puncture. Specifically the present device provides a means by which short sutures in a circular cuff on each end of a graft tube use stored energy to curve through tissue of an adjacent lumen wall from inside the graft tube thus connecting it to the lumen wall in which it is concentrically located with the object of providing a conduit for blood to flow inside, rather than outside a diseased vessel that has become so occluded it can no longer perform its function. The device can also provide a scaffold for growing living linings inside the vessel or function as a dialysis shunt.

2. Prior Art

Prior Art References:

| US Patent Number, | Year, | Name |
|---|---|---|
| 3,334,629 | 1967 Aug. 08 | Cohn |
| 3,494,006 | 1970 Feb. 10 | Brumlik |
| 4,503,569 | 1985 Mar. 12 | Dotter |
| 4,733,665 | 1988 Mar. 29 | Palmaz |
| 4,893,623 | 1990 Jan. 16 | Rosenbluth |
| 5,002,563 | 1991 Mar. 26 | Pyka |
| 5,197,978 | 1992 Mar. 30 | Hess |
| 5,163,955 | 1992 Nov. 17 | McNamara |
| 5,662,700 | 1997 Aug. 02 | Lazarus |
| 5,810,870 | 1998 Sep. 22 | Myers |
| 6,652,570 | 2003 Nov. 25 | Smith |
| 6,264,684 | 2001 Apr. 24 | Banas |
| 7,713,215 | 2010 May 11 | Shriver |
| 7,771,422 | 2010 Aug. 10 | Shriver |

Atherosclerosis is a disease that afflicts about 20 million people in the United States; more than any other life threatening disease. The Greek word "athero" means "gruel" and "sclerosis" "hardening," so the disease is also known as "hardening of the arteries." Today this gruel is often called "plaque," and may produce fatty deposits, hard calcium deposits, or interact with clotted blood in producing aneurysms. Regardless of the nature of the occlusion, its effect is to occlude the artery making it incapable of performing its function of delivering oxygen-carrying blood to muscles and organs beyond the occlusion. When the brain or heart is oxygen-deprived, death or impairment occurs rapidly. When muscles of the lower body are oxygen-deprived, death is slower but half die within 10 years. There may or may not be pain symptoms in the legs and gangrene may be the first clear indication. Amputation is often required to avoid death. Atherosclerosis may be treated by diet and drugs but patients often do not follow diets and the effects of tobacco smoke are irreversible even if the person stops smoking.

The gold standard treatment is a bypass graft with its ends "grafted" to the artery on each side of the occlusion thus carrying blood around it. A bypass graft remains functional about 7½ years on average. Despite being the "gold standard," the problem with bypass grafts is they require surgery to place them in the body. Surgery is risky and debilitating. For instance, a coronary bypass procedure starts with splitting the sternum and pulling apart the rib cage in what was called the "bloody eagle" torture in earlier centuries. This is just to allow the surgeon's hands to get in the body to suture one or more bypass grafts around occlusions. There are so-called "Da Vinci" machines that assist the surgeon's fingers in remaining steady enough to place coronary bypasses through openings in the chest, but this machine is applicable in a limited number of circumstances. Open surgery to place a bypass graft in the lower body is not quite as debilitating as that for opening the chest but is risky and involves a long recovery time in comparison to percutaneous entry through a skin puncture. The catheter-based methods of entering the body through a skin puncture go through the occlusion rather than going around it. A balloon is inflated in the occlusion to open it, but the occlusion starts to close (restenosis) when the balloon is removed. To keep the occlusion propped open, stents were developed in the 1990s. Stents are wire mesh tubes that increase the length of time balloon treatments last in coronary artery applications. But in the longer arteries and occlusions of the legs stents do not improve the duration of a balloon treatment. Occlusions grow back through openings in the wire mesh and stents tend to fracture in the dynamic leg environment. Thus the duration of balloon and stent treatments in the legs is about 2½ years on average. Bypass grafts last about 7½ years on average, or about 3 times the duration of balloons with or without stents. Balloon treatments have largely replaced bypass graft treatment as surgery now required to place bypass grafts is a last resort after many balloon failures, so used in only about 20% of the peripheral artery cases. The problem of the occlusion growing back through the open mesh in stents was dealt with in 2005 by placing a substance on the stent to resist that growth. But the drug has created other problems, like causing blood clots that sometimes get caught in an artery to the brain and cause a stroke from loss of blood to the brain. The latest "fix" for stents is placing graft tubes on them in so-called stent grafts thus closing open holes in the mesh and sealing off the diseased tissue. These stent grafts have included ePTFE and heparin bioactive surfaces to inhibit intimal hyperplasia and regrowth of the occlusion. But occlusions tend grow back at the ends of stent grafts. Whether the addition of a graft to the stent will avoid the problems of the stent fracturing in the dynamic environment of the legs has not yet been determined nor has the duration of this treatment. The stent graft includes metal so is not biodegradable and thus not useful in combination with tissue engineered vessels (TEV) that are graft tubes made from the patient's own body cells. The TEVs duplicate the structure of the artery wall's three layers, including those of muscle and elasticity and vascular endothelial growth factors are used with these TEVs. But as long as surgery is needed to place them in the body, their use will be limited to a fraction of the 20% of cases treated by surgery. There are catheter-based devices other than balloons, stents and stent grafts for opening occlusions. They utilize grinding, freezing, jetting fluid, lasering, etc., to remove the various types of deposits after entering through a skin puncture. They are generally effective in removing the occlusion but the occlusions grow back just as fast as when treated with balloon angioplasty. So these removal devices do not appear to increase the duration of balloons with or without stents. However they may be used in combination with a device for placing a bypass graft through a skin puncture. Data from peer-reviewed articles may be summarized as: bypass grafts, whether artificial or a vein from the patient's own body, last about 50% longer than balloons and stents in the short coronary arteries and about 300% longer in the peripheral arteries of the lower body. Restenosis, or regrowth of the occlusion, is faster in longer occlusions of the legs. Also stents tend to fracture in the dynamic environment of the legs. Stents that elute drugs to prevent regrowth of occlusions through openings in the mesh create problems such as blood clots. Closing the mesh opening by combining a graft tube with a stent causes the occlusions to regrow around the ends of the stent grafts and does not solve the problem of metal stents fracturing in the legs. Thus, though the percutaneous methods lack the effectiveness of the bypass graft, skin punctures are so much safer and less debilitating than open surgery that balloons and stents have become the preferred treatment for coronary and peripheral arteries. If the safety of skin punctures can be combined with the effectiveness of bypass grafts in a new device and procedure, it would likely replace many of the other means of treating hardening of the arteries.

Two patents have been issued to the present inventor for devices that place bypass grafts around the occlusion in both coronary and peripheral arteries. There also appears to be a need for a device that provides the means of placing a graft tube inside the vasculature after the occlusion is removed, perhaps providing a more effective or safer treatment than a bypass graft around the occlusion. Furthermore it would be usable in combination with, and provide a scaffold for placing TEVs inside the vasculature and biodegrading as the TEV grows into the lumen wall. To accomplish these objects, the graft tube must avoid the means used by stents to attach to lumen walls, namely by pressure exerted throughout their length, and should be capable of accomplishing the object when constructed entirely of biodegradable material.

These objects are not accomplished by balloons, stents, eluting stents, and stent grafts, alone or combined.

The present device will suture a graft tube inside the artery after the occlusion is removed. Specifically, the graft tube is not a stent or stent graft. A stent graft combines stent and graft tube that connects to the lumen wall by the pressure exerted by the metal stent throughout the length of the stent graft. Patents for stents and for stent grafts are cited as prior art, but none attach to the lumen wall by sutures. All attach by exerting pressure from the expanding stent against lumen walls. Therefore there is only the object of stents that could be considered prior art but no stent graft use the means of attaching to lumen wall by sutures. It does not require a detailed analysis of each patent to show how the basic means of attachment by stents is different from the means of attachment by sutures but examples of stent patents are included.

The only prior patent found using a means other than stents to attach a graft tube to a lumen wall from inside the lumen is the Lazarus patent 5,662,700 in which he describes an artificial graft and implantation method where a prosthesis graft is placed inside a blood vessel which may be an artery. He refers to aneurysms as weakened blood vessels creating a need for prosthesis such as an artificial vessel or graft. The device is described as having one or more staples (sharp hooks) attached to each end of the intraluminal graft to prevent it from migrating. Thus the objective is the same as that of the present invention, namely to connect the ends of a graft tube to the lumen wall in which it is concentrically located without using a stent. Lazarus utilizes hooks pushed into the lumen wall on the ends of a graft tube rather than along its entire length to hold it in place. He cites prior devices that used hooks as the means of attaching one surface to another. Since Lazarus does not mention any means for removing or pushing aside occlusions such as fatty material, blood clots or calcified material in order for the device to be put in place, it may be assumed his device is intended for coronary artery applications as his device might be able to push aside some short coronary occlusions but not the long occlusions typically found in the long peripheral arteries of the legs. Also, the means of attaching by hooks may be tolerable in coronary arteries as they are surrounded by pericardial fluid whereas peripheral arteries are surrounded by muscle tissue, nerve and vein which could be injured by hooks moving outside the lumen wall. The hooks will prevent the graft tube from moving in the direction the hooks are pointed but not in the direction the points of the hooks are pointed unless the graft tube is stretched tautly between hooks.

Cohn, in 3,334,629 describes a means of attaching a device inside a blood vessel in which extensible vanes having sharp teeth on the ends engage the interior walls of a blood vessel for the object of keeping it fixed in place. This has similarities to the Lazarus device in the use of hooks but not to the proposed device.

Brumilik, in patent 3,494,006 describes a fastening device intended as an improvement over a "velcro" type fastener in that only one surface is provided with fastener means, the other being permanently attached to elongated bodies having at least one barb on the free end which is intended to penetrate and lodge in the article to which adhesion is desired. This is not the means proposed with the present device, namely using sutures for the connection.

Prior devices by the present inventor are for placing a bypass graft around the occlusion as done in open surgery and not for placing the graft through the occlusion concentrically inside the diseased vessel. In patent 7,771,442 a combination seal and suture is described where stiff sutures are located in hollow sutures in the longitudinal portion of a seal attached to the end of a bypass graft. An inflatable balloon with push rods on its circumference is used to push the sutures out of the longitudinal section of the seal as the flange on its end is held by a holding balloon. The sutures are driven through the artery wall and into the flange located inside the artery lumen. The stiff sutures move forward in the direction they are pointed by the hollow sutures in which they are located. There is no tunnel in the flange for the stiff suture to enter, though there may be a trench to hold the stiff suture while it punctures a tunnel. This method attaches the seal (and the graft tube with a seal on each end) to the artery in fluid-tight connections on each side of the occlusion.

That invention requires another invention by Shriver, 7,713,215, which describes a device for piercing and dilating tissue to make an opening in the side of the artery for the seal flange to enter the lumen of the artery and dilate a tunnel outside the artery in which to place the graft. The flange is pushed through this opening in the side of the artery to expand inside the artery lumen and thus fit against the lumen wall to receive the stiff sutures pushed from the stem section of the seal after they pass through the tissue on the edge of the opening in the side of the artery.

The present invention utilizes a circular cuff rather than a seal and the cuff is entirely inside the artery rather than half in/half out of the artery as are the stem and flange portions of the seal. The present invention does not require an opening in the side of the artery because the graft tube, with circular cuffs on each end, is concentrically within the artery lumen. Short sutures, manufactured in a particular configuration are forced into a tunnel in the circular cuff thus storing energy in them prior to their use. They are pushed out of the tunnel and the stored energy is released causing the short suture to curve through tissue in the lumen wall and return to the circular cuff. The circular cuff has a second tunnel for the short sutures to enter and lodge in. The sutures hold both ends of the graft tube in place in the artery lumen, thus providing a conduit of biodegradable or non-biodegradable material lining the diseased section of artery or vein. The occlusion is removed by one of the standard devices for that purpose before the graft tube is placed.

OBJECTS AND ADVANTAGES

Accordingly, there is no prior art with the object or means of entering the body percutaneously and attaching a graft tube to the lumen wall by means of sutures at the ends of the graft tube without the use of hooks or metal stents throughout the length of the graft tube. The present invention uses a means of attachment that prevents migration of the graft tube in both directions while avoiding the risk of sharp hooks extending beyond the artery wall and injuring adjacent nerve and/or vein located in the same canal with the artery in the legs thus providing the following unique advantages:

1. provides a conduit for the flow of blood through one or more sections of diseased vasculature which have become occluded by atherosclerotic disease and thus unable to accomplish the function of passing blood;
2. provides an impermeable barrier to the regrowth of occlusive material that is removed before placing the graft tube concentrically in the diseased vessel, with suture connections in healthy tissue distal and proximal to the diseased tissue;
3. provides the same type of graft and sutures that have proven to be substantially more effective than balloons and stents when placed surgically;
4. provides connections to the lumen wall by sutures that have a history of use in surgical procedures that suggests they will not induce the body to react to them with hyperplasia or other responses typically induced by foreign bodies such as hooks or stents in the body;
5. provides connections to the lumen wall that loop through the lumen wall and back into the device thus avoiding injury to adjacent body parts that might be injured by sharp hooks that extend through the lumen wall as sharp points that last indefinitely as they do not loop back into the device or biodegrade;
6. provides a conduit within the diseased vessel thus avoiding the complication of providing a tunnel for the conduit outside the vessel and openings in the side of the vessel for connection of the conduit around the occlusion;
7. provides a biodegradable scaffold to protect tissue made of cells from the patient's body that would be injured by being the conduit immediately but will grow into being a conduit for blood while the scaffold is serving as the conduit and also being absorbed by the body.

SUMMARY OF THE INVENTION

A graft tube is percutaneously placed in a vessel lumen and attached to the lumen wall by loops of suture material. The short sutures are made of material with shape memory in the shape of a loop with a sharp and a blunt end then forced into tunnels having a straight and a curved segment. The tunnels are located in tunnel housing sections that are part of circular cuffs attached to each end of a graft tube. The short sutures are pushed out the first tunnels by push rods, pierce and loop through the adjacent lumen wall and then enter second tunnels where the short sutures are lodged. The suture loops hold the circular cuffs on ends of the graft tube in place. The graft tube may serve as the conduit for blood flow or may be made of biodegradable material and thus serve as a temporary scaffold for a tube of engineered tissue grown from the patient's body. The circular cuff may be increased in circumference as a means of becoming adjacent to lumen walls and/or increase blood flow, possibly reduce hyperplasia and edge occlusion. A delivery catheter, holding balloons, and push rods are also revealed for delivering the graft and pushing the sutures in place. The present device is intended for use after occlusions are removed by standard FDA-approved devices.

| Key | |
|---|---|
| 1. | Tunnel housing section |
| 2. | First tunnel |
| 3. | Second tunnel |
| 4. | In port |
| 5. | Out port |
| 6. | Through port |
| 7. | End port |
| 8. | Short suture |
| 9. | Tunnel lining |
| 10. | Sharp end |
| 11. | Blunt end |
| 12. | Circular cuff |
| 13. | Shroud |
| 14. | Holding disc |
| 15. | Inside holding catheter |
| 16. | Key |
| 17. | Guidewire |
| 18. | Groove |
| 19. | Holding balloon |
| 20. | Push rod |
| 21. | Push rod catheter |
| 22. | Keyway |
| 23. | Support |
| 24. | Outside holding catheter |
| 25. | Delivery catheter |
| 26. | Graft tube |
| 27. | Artery |
| 28. | Lumen wall |
| 29. | Undulating wire |
| 30. | Push rod balloon |
| 31. | Additional circular cuffs |
| 32. | Indent |
| 33. | Barb |

DETAILED DESCRIPTION OF THE INVENTION

Having thus described the figures, methods in accordance with the present invention are now described with reference thereto. It should be understood that steps described for each process may be omitted or the order changed or performed simultaneously without deviating from the spirit or scope of the invention. The following description should be read with reference to the drawings, in which the elements in different drawings are numbered in like fashion. The drawings, which are not necessarily to scale, depict selected embodiments and are not intended to limit the scope of the invention. Examples of construction, dimensions, materials, and manufacturing processes are provided for various elements but merely as a reflection of current manufacturing practices regarding processes and materials. Those skilled in the art will recognize that many of the examples provided have suitable alternatives in materials, manufacturing processes and specific configurations which may be utilized now and in the future to produce equivalent means.

Figure 1A:
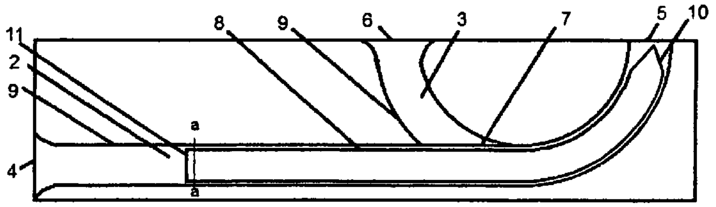
FIG. 1*a* shows the tunnel housing section with first tunnel, second tunnel, ports, smooth lining and short suture forced into shape of first tunnel.

FIG. 1*a* shows housing section 1 which may be integral to or attached to circular cuff 12 depending on the materials and methods used in their manufacture. First tunnel 2 has in port 4 and exit port 5 and a smooth tunnel lining 9 which may be the same or different metal or polymer material as tunnel housing section 1, as in this example. In port 4 may be flared as shown. Second tunnel 3 has through port 6, which also may be flared, and end port 7 which may be a dead end or lead back into first tunnel 2 depending on whether in adjacent or same plane with respect to in port 4. The same smooth tunnel lining 9 is shown for second tunnel 3. An example of short suture 8 with sharp end 10 and blunt end 11 is shown in first tunnel 2. First tunnel 2 must have a straight section at least as long as short suture 8 and must curve in the shape of short suture as originally biased during manufacture to exit port 5 on the same side of tunnel housing 1 as through port 6. Alternative configurations are possible so long as exit port 5 and through port 6 are on the outside width of the tunnel housing. With certain manufacturing methods, such as injection molding and certain materials, the tunnels may not require linings. Linings may be made of a stainless steel hypotube, nickel-titanium alloy or other metal or be made of a biodegradable or non-biodegradable polymer. Linings and short sutures may be coated with PTFE or other slippery substance to reduce intermolecular resistance when sliding.

Figure 1C:
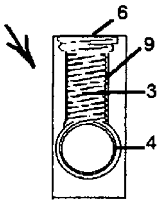
FIG. 1*c* provides a width view of the tunnel housing section with a tunnel lining of wound wire.
Figure 1B:
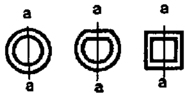
FIG. 1*b* shows examples of alternate cross-sections of first and second tunnels and short suture.

FIG. 1*b* shows examples of cross-sections of first tunnel 2 and short suture 8. The cross section may be any shape as long as it is the same for short suture 8, first tunnel 2 and second tunnel 3.

FIG. 1*c* shows the first tunnel 2 and second tunnel 3 in tunnel housing being in one plane. More force can be transmitted from blunt end 11 to sharp end 10 when the two ends are in the same plane than if only a vector of that force is transmitted when the ends are in different planes. This does not prevent placing the tunnels in adjacent planes, but in this figure both tunnels are shown in one plane. Also a wire wound tunnel lining 9 is shown as an example of a different type of lining than shown in FIG. 1*a*.

Figure 2A:
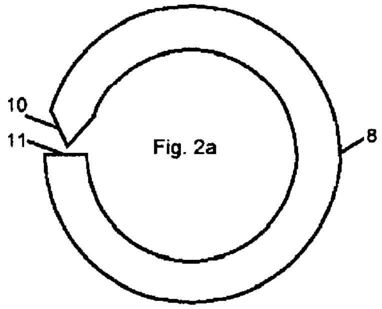
FIG. 2*a* shows an example of a short suture having a sharp end, a blunt end and circular shape to which it will return after being deviated in first tunnel.

FIG. 2*a* shows an example of short suture 8 manufactured as circular. Short suture 8 has blunt end 11 and sharp end 10. Sharp end 10 is shown as a point on the centerline (as with a pencil point), but a truncated section like a chisel point may also be used as sharp end 10. The suture is made of material with shape memory as with spring steel, nickel titanium alloy metal or polymer material that will cause it to return to its original shape after it has been forced into another shape such as that imposed by first tunnel 2. When short suture 8 is forced into the straight part of first tunnel 2 energy is stored which is released as it is pushed out of first tunnel 2 causing it to curve through tissue of the adjacent lumen wall. Further pushing sends short suture 8 into second tunnel 3. The short suture may have incisions made on its surface to create barbs 33 their purpose being to prevent short suture 8 from moving back once advanced. The shape of end port 7 may be made to hold sharp end 10 by friction or it may be an opening into the side of first tunnel 2.

Figure 2B:
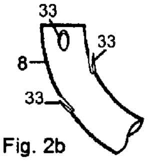
FIG. 2*b* shows an example barbs incised on a section of a short suture.

FIG. 2*b* shows barbs 33 as produced by incisions made in the direction of sharp end 10 on the surface of short suture 8.

Figure 2C:
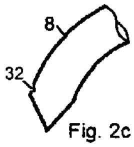
FIG. 2*c* shows an example of an indent on the outside circumference of a short suture.

FIG. 2*c* shows indent 32 on the outer circumference of short suture 8 which can be used to push short suture 8 into an opening on the side of first tunnel 2 with push rod 20.

Figure 2D:
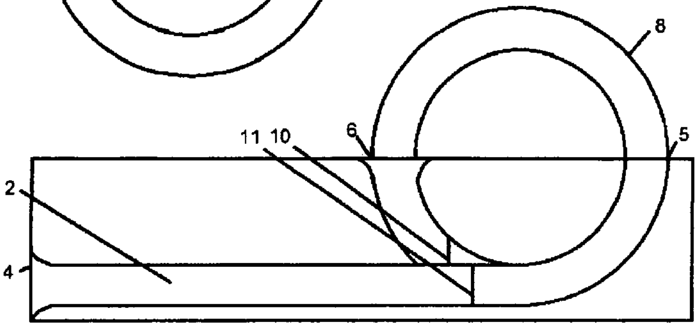
FIG. 2*d* shows an example of a short suture after being pushed out of first tunnel and into second tunnel which have no linings in this example.

FIG. 2*d* shows short suture 8 after it has been pushed out of first tunnel 2 and into the second tunnel 3. It resumes its original shape as it emerges from exit port 5, pierces any tissue adjacent, such as the lumen wall of an artery 27, vein or other natural body, and either lodges with sharp end 10 in second tunnel 3 and blunt end 11 in first tunnel 2 or may be urged into an opening in the side of first tunnel 20 by push rod 20 engaging indent 32.

Figure 2E:
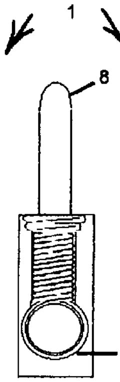
FIG. 2*e* shows the same short suture of FIG. 2*b* in a width view as being in one plane and in a tunnel with a wire wound lining.

FIG. 2*e* shows the first tunnel 2 and second tunnel 3 in one plane with short suture 8 in line.

Figure 2F:
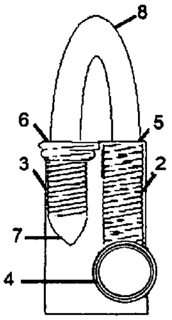
FIG. 2*f* shows an alternative configuration of first and second tunnels in adjacent planes with a short suture manufactured to similarly be twisted into adjacent planes.

FIG. 2*f* shows short suture 8 as manufactured with a bias that diverts it from one plane into another to conform to the arrangement of the first tunnel 2 and second tunnel 3 in adjacent planes. No advantage is known for this configuration over the single plane but the claims do not preclude this or other configurations and a chisel point may aid in moving sharp end in direction opposite flat face.

Figure 3A:
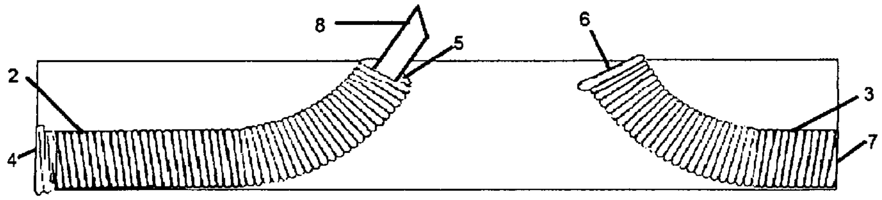
FIG. 3*a* shows an alternate configuration for first and second tunnels with a tunnel lining of wound wire and a short suture manufactured to conform to this configuration and having a chisel point sharp end.

FIG. 3*a* shows an alternate configuration for first tunnel 2 and second tunnel 3 with short suture 8 manufactured with an alternative configuration as emerging from first tunnel 2.

Figure 3B:
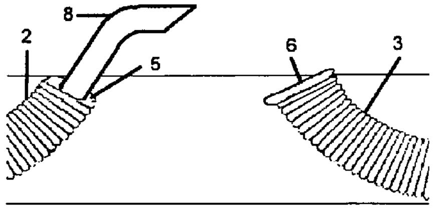
FIG. 3*b* shows a detail view of the same short suture pushed further out of first tunnel.

FIG. 3*b* shows a restricted view of the alternative configuration shown in FIG. 3*a* with short suture 8 having been pushed farther out of the first tunnel 2.

Figure 3C:
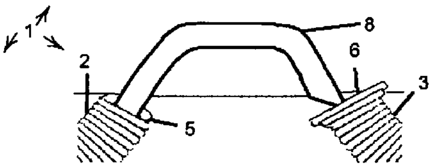
FIG. 3*c* shows a detail view of the same short suture entering the second tunnel.

FIG. 3*c* shows a still more restricted view of the alternative configuration shown in FIG. 3*a* with short suture 8 having been pushed almost into second tunnel 3.

Figure 4A:
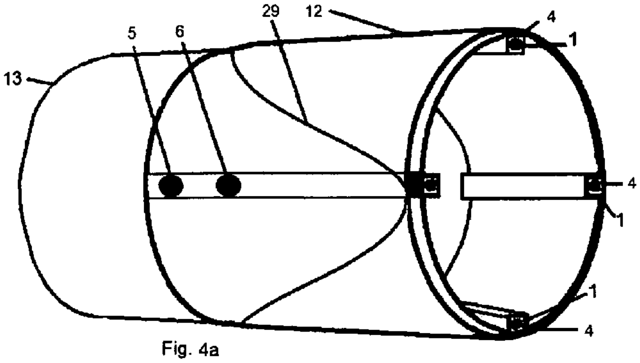
FIG. 4*a* shows a circular cuff with 4 embedded tunnel housing sections having an angular shape and a shroud for connecting to a graft tube.

FIG. 4*a* shows circular cuff 12 with shroud 13 for connecting to an end of graft tube 26 and four [of one or more] tunnel housing sections 1. Circular cuff 12 is made of a polymer that will attach to both the material of circular cuff 12 and graft tube 26. The material may allow circular cuff 12 to be expanded to a larger circumference and may utilize an undulating wire 29 of steel or polymer to assist the material used to manufacture circular cuff 12 to remain at an expanded circumference or return to any other predetermined circumference. Entry port 4 and through port 5 are shown on the same side of circular cuff 12 which is farthest from its centerline and thus adjacent the lumen wall of artery 27 in which circular cuff 12 is concentrically located. Tunnel housing sections 1 are shown with square corners and about half protruding into the open area inside the inner diameter of circular cuff 12 though corners may be rounded.

Figure 4B:
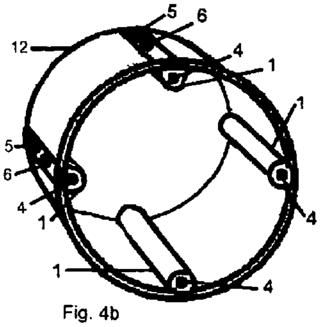
FIG. 4*b* shows a circular cuff with shroud removed so the alternative rounded tunnel housing sections can be seen pointing in another direction.

FIG. 4*b* shows circular cuff 12 without showing shroud 13 but with rounded corners on four tunnel housing sections 1. The number of tunnel housing sections can be one or more, but four are used in these figures.

Figure 5A:
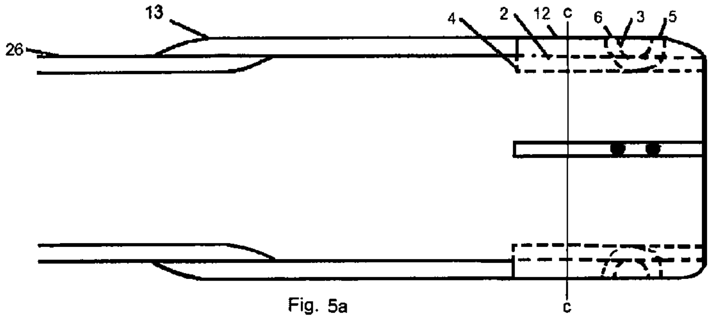
FIG. 5*a* shows the cross section of the circular cuff of FIG. 4*a* with embedded angular tunnel housing sections.

FIG. 5*a* shows a cross section of circular cuff 12 with shroud 13 overlapping graft tube 26 and dotted outlines of tunnel housings 1, first tunnels 2, second tunnels 3, exit port 5 and through port 6. Circular cuff 12 and graft tube 26 may or may not be attached at the factory because the length of graft tube 26 required for each person's particular characteristics is so variable, and an accurate fit is required so it may be impractical to have graft tubes made in every possible length. Therefore the shroud may be used to accommodate this practical circumstance of connecting after determining the length of graft required for a particular application, which can include making segments of graft tube 26 each with ends attached to an additional circular cuff 31 so that a graft tube of such segments appears as one graft tube 26 with additional circular cuff 31 at location between distal and proximal ends of the contiguous segments. This is done with long graft tubes which may have proximal end at upper thigh and distal end at mid or lower calf thus attaching to large femoral and small popliteal artery of substantially different diameters which may require different diameters of proximal, and distal circular cuffs 12 and additional circular cuff 31 and graft tube 26. The overlap of shroud 13 and graft tube 26 is needed for strength when a strong adhesive such a mussel glue or epoxy is applied to hold them together. A butt joint is desirable and can be made as strong as an overlapping joint, e.g. Advanced Polymers, Inc. provides a method of bonding with their Split Die Thermal Bonder that they claim makes butt welds as strong as those obtained with overlapping joints and that it is usable in an operating room. If so, that or a similar process may be used to make a butt joint between shroud 13 and graft tube 26 or between circular cuff 12 and graft tube 26. The material for the circular cuff may be biodegradable or non-biodegradable as required for the application.

Figure 5B:
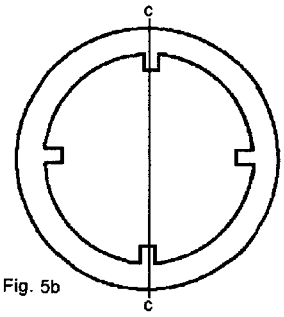
FIG. 5*b* shows a cross sectional view of the circular cuff in FIG. 5*a*.

FIG. 5*b* shows a cross section of circular cuff 12 having four tunnel housing sections 1 with square corners.

Figure 6A:
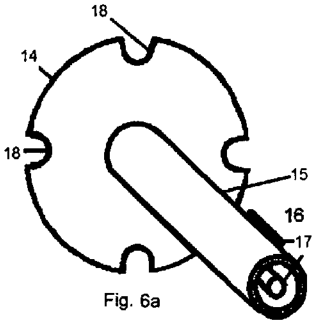
FIG. 6*a* shows a holding disk on a distal inside holding catheter with an alignment key and a guidewire inside the catheter.

FIG. 6*a* shows one type of holding member being a holding disc 14 made of rigid material with four rounded channels 18 as example of a plurality of channels that are slidably larger than the corresponding four rounded tunnel housing sections 1 of circular cuff 12 shown in FIG. 4*b*. This allows holding disc 14 to pass through circular cuff [12] and then be rotated on the opposite side of circular cuff 12 so the grooves are not aligned with the tunnel housings but hold circular cuff 12 by tunnel housing sections 1 when push rods 20 are forced into first tunnel 2.

Figure 7B:
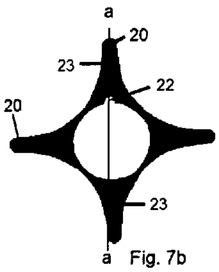
FIG. 7*b* shows a cross section of the push rods, supports, and a keyway for aligning the catheters.
Figure 8A:
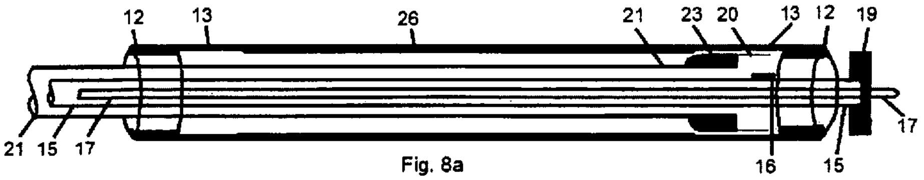
FIG. 8*a* shows a guidewire inside the distal holding catheter, a key, the push rod catheter with push rods and supports inside a graft tube connected to circular cuffs with shrouds.
Figure 8B:
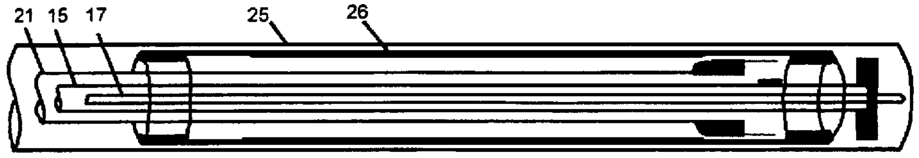
FIG. 8*b* shows the components of FIG. 8*a* inside a delivery catheter which is an alternative component for delivering those components.
Figure 8C:
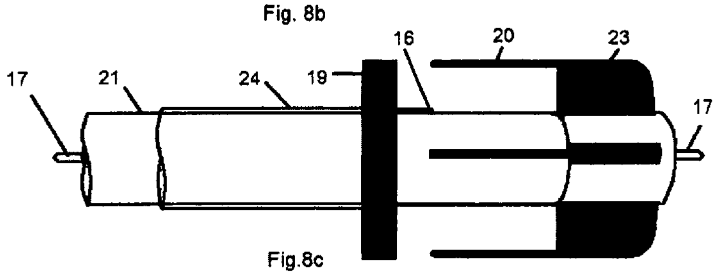
FIG. 8*c* shows the push rods mounted on a push rod catheter and pointing in the proximal direction toward a proximal [outside] holding balloon and catheter which is slidably larger than the push rod catheter and in position to push in the opposite direction [as] the push rods are being pulled.

Key 16 is a longitudinal protrusion, shown here on inside holding catheter 15 near where holding disc 14 is mounted and is shown mounted on push rod catheter 21 in FIG. 8*c*. Key 16 fits in keyway 22, which is a longitudinal dent shown in push rod catheter 21 in FIG. 7*b* located under push rod support 23 to align push rods 20 to first tunnels 2 before holding disc 14 is in circular cuff 12 before being moved to the distal side of circular cuff 12. At the distal end shown here, keyway 22 is located in push rod catheter 21, and it will be seen that at proximal site keyway 22 is located in outside holding catheter 24 as shown in FIG. 8*c*. So key 16 and keyway 22 are engaged while holding members, either holding disc 14 or holding balloon 19 are within circular cuff 12 and disengaged when inside holding catheter is pushed through circular cuff 12 thus allowing holding disc 14 to be rotated by rotating inside holding catheter 15. Inside holding catheter 15 is located inside push rod catheter 21 at distal end of graft tube and outside holding catheter 24 is located outside push rod catheter 21 at proximal end of graft tube as first shown in FIG. 8*c*. There is no functional difference between inside holding catheter and outside holding catheter but the physical difference in diameter requires the key way to be on the outermost of the two—which is different at distal and proximal ends. Guidewire 17 is shown in inside holding catheter 15 as it is required to advance holding catheter 15 which is the smallest catheter.

Figure 6B:
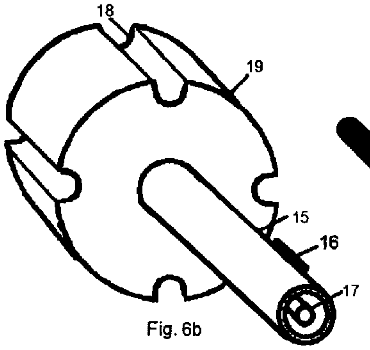
FIG. 6*b* shows a holding balloon on a distal [inside] holding catheter with an alignment key and a guidewire inside the catheter.

FIG. 6*b* shows holding balloon 19 with grooves 18, inside holding catheter 15, key 16 and guidewire 17. Holding balloon 19 is an alternative configuration of holding member used in the same way as holding disc 14, but in addition holding balloon 19 can be used to grip for delivering and to increase the circumference of circular cuff 12 when the predetermined situation with the patient requires this. For this situation, circular cuff 12 is made of an expandable polymer. Thus circular cuff 12 can be expanded by inflating holding balloon 19 within the inside diameter. The shape memory of the polymer material of which circular cuff 12 is made will determine what size it will assume after expansion and physicians will choose the size they desire in a particular application. For instance, the blood vessel being treated may have been enlarged by an aneurysm and may have lost most of its elasticity. Expanding circular cuff 12 to be of that diameter would be required to become contingent with it but after being connected to the lumen wall, the physician must choose what circumference circular cuff 12 should return to [or remain at] and select a circular cuff 12 of the appropriate material or decide whether there is a need for a circular cuff 12 that expands. This decision further depends on whether he/she considers the situation one where holding balloon 19 can be used as the delivery member without a delivery catheter. As delivery member holding balloon 19 grips second circular cuff 12 by being inflated in its opening to enable operator to push holding balloon 19 on its catheter to advance second circular cuff 12 to the preselected distal location in the vessel lumen. When holding balloon 19 so changes the circumference of the circular cuff, a push rod balloon 30 must be the push rod support member used that can match the circumference change.

Figure 6C:
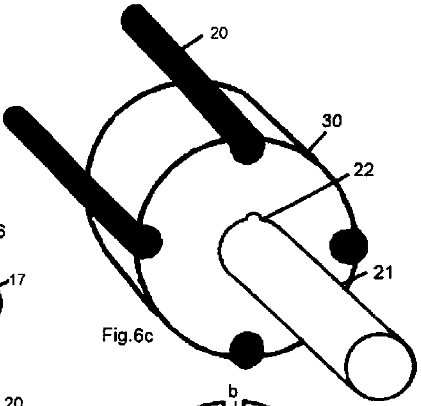
FIG. 6*c* shows a push rod balloon with push rods mounted on a push rod catheter with a keyway.

FIG. 6*c* shows an inflated push rod balloon 30 made of compliant material to enable expansion and non-compliant material on circumference to resist the torque imposed by push rods 20 located where grooves 19 are located to align with tunnel housing sections 1 and embedded in the outer circumference with the aid of adhesives and/or heat treatment. The push rod catheter 15 is also shown with keyway 22. The push rods are placed to extend away from the push rod support members, in the distal or proximal direction depending on whether push rod support members are for entering circular cuffs on distal or proximal ends of graft tube.

Figure 7A:
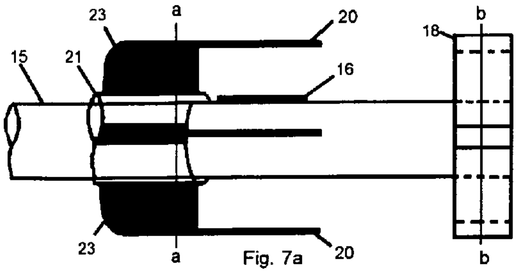
FIG. 7*a* shows push rods with supports on a push rod catheter sliding on a distal holding catheter which is attached to a holding balloon.

FIG. 7*a* shows push rods 20 on support 23 made of rigid stainless steel or polymer. Supports 23 extend from each push rod to where they are attached to push rod catheter 21 at a right angle when support member is rigid as shown here and around circumference of balloon when support member is an inflatable balloon as shown in FIG. 6*c*. With either support member each push rod is in alignment with an entry port of tunnel housing when key 16 and keyway 22 are aligned. Inside holding catheter 15 has distal holding balloon 18 mounted on it and is inside push rod catheter 21. The preferred procedure is to approach the "distal" circular cuff first but this is not a requirement of the device. An alternative procedure is described with FIG. 8*c* and in FIG. 8*d* the outside holding catheter 24 is shown as outside of push rod catheter 21 rather than being inside as shown here.

FIG. 7*b* shows a cross section view of the distal holding balloon 19 and distal holding disc 14 has the same cross-section. The cross-section view shows keyway 22 between supports 23.

Figure 7C:
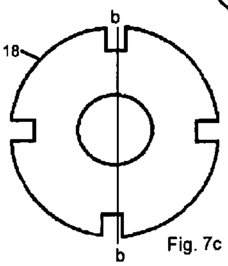
FIG. 7*c* shows a cross section of the distal holding balloon.

FIG. 7*c* shows a cross-section view of holding disc 18 with angular corners.

FIG. 8*a* shows the concentricity of the various tubular elements at distal attachment site. Guidewire 17 is the smallest and used to guide the others. Being the distal site, inside holding catheter 15 is next larger in size and having been used to advance distal holding balloon 19 (shown here) or distal holding disc 14 beyond circular cuff 12. The next largest is push rod catheter 21 which is slidably smaller than graft tube 26 with shroud 13 attaching it to circular cuff 12. When push rods 22 are advanced or withdrawn, either holding member, holding disc 14 or holding balloon 19 is moved in proximity to guard against push rods 20 "catching" or piercing graft tube 26.

FIG. 8*b* shows the same device components as FIG. 8*a* plus (optional) delivery catheter 25 which would be used to deliver the other components and protect them through a calcified artery and possibly in other circumstances as well. Delivery catheter 25 is removed by withdrawing it while second circular cuff 12 is gripped on inside opening by inflated holding balloon 19 on inside holding catheter 15 keeping second circular cuff 12 and graft tube 26 in place.

FIG. 8*c* shows push rods 22 attached to push rod catheter 21 by rigid support member with push rods 22 pointing in the proximal direction and thus ready to repeat the attachment procedure at the proximal end of graft tube 26 after short sutures 8 have attached circular cuff 12 to the lumen wall 28, e.g. artery 27 at the distal end of graft tube 25. The lumen wall can be an artery 27, a vein or other body tube. The holding member, holding disc 14 or holding balloon 19 used at the proximal end is shown on a proximal outside holding catheter 24 that is slidably larger than push rod catheter 21. Holding balloon 19 is needed as holding member if circular cuff 12 is expanded. The procedure for pushing short sutures 8 into a lumen wall 28, such as artery 27, is similar at proximal and distal ends of graft tube 26. Further, the procedure at the proximal end includes using the push rods 22 to pull short sutures 8 rather than pushing them as at distal end. At proximal end entry port 4 of first tunnel 2 is placed on the distal side of circular cuff 12, and push rods 20 mounted to point as shown here. Holding member, either holding balloon 19 or holding disc 14 is mounted on outside holding catheter 24 which is slidably larger than push rod catheter 15 and pushed against push rods 22 rather than pulled. This is a complication in describing the device so the point is made here once without repeating it [with every element that is reversed].

Figure 8D:
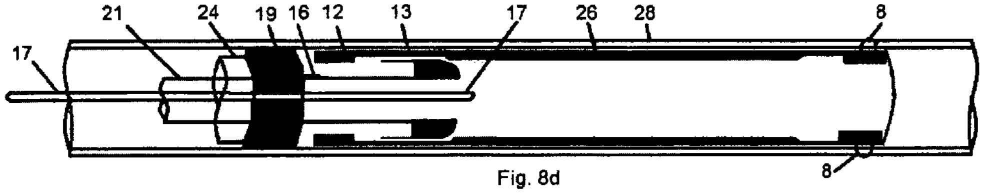
FIG. 8*d* shows the artery (one type of lumen wall) to which the circular cuff has been attached by short sutures on the distal end and the proximal push rod and holding balloon are in position to do the same on the proximal end.

FIG. 8*d* shows the relationship of push rods 22 and proximal holding balloon 19 when making the proximal connection to the lumen wall. Shroud 13 is of such size as not to interfere with the operation on the push rods 22 and in ports 4. Short suture 8 loops are shown already attached on the distal end. Outside holding catheter 24 is shown outside of push rod catheter 21 at the proximal end whereas inside holding catheter 15 is inside push rod catheter 21 at the distal end, as shown in FIG. 7*a*. This is no functional significance to this but keyways must be on the larger catheter so keyway 22 is on outside holding catheter 24 at proximal end and on push rod catheter 21 (which is larger than inside holding catheter 15) at distal end.

Figure 9A:
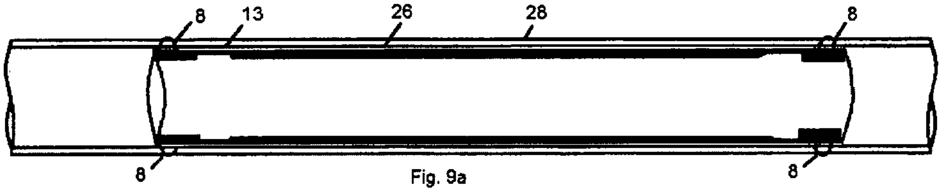
FIG. 9*a* shows circular cuffs attached to the inside of the artery by sutures on distal and proximal ends of the graft tube and all other device components have been removed.

FIG. 9*a* shows graft tube 26 and circular cuff 12 fastened to lumen wall 28 on proximal and distal end. Graft tube 26 may be constructed to taper from proximal to distal end with all device components made accordingly smaller for use on the distal end. The graft tube may be covered by ePTFE, and/or tissue engineered vessels, or have a heparin bioactive surface or endothelial growth factor applied. These coverings do not change the device elements or their mode of operation. However a particular type of covering, such as a tissue engineered vessel or TEV may be used to replace graft tube 26 after it has served as a scaffold while the TEV grows together with the lumen wall. In that case shroud 13, circular cuffs 12 and short sutures 8 are made of biodegradable material.

Figure 9B:
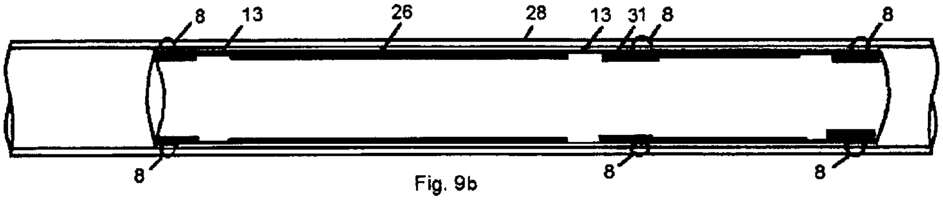
FIG. 9*b* shows the shroud next to an additional circular cuff that has been used to place short suture between short sutures on distal and proximal ends of a graft tube.

FIG. 9*b* shows the results of using additional circular cuff 31 in cases where graft tube 26 must be very long to treat a particularly long occlusion, circular cuff 31 is not visible in this cross section view but shroud 13 may be seen between the ends of graft tube 26 as can short suture 8 which came out of additional circular cuff 31.

What is claimed is:

1. A device for suturing a first circular cuff and a second circular cuff attached to ends of a graft tube, to lumen walls when concentrically located in the lumen after entering the vascular system through a skin puncture comprising, a. a first circular cuff and a second circular cuff each having a shape of a wide ring or cuff on a sleeve, each being continuous with or attached to one or more tunnel housing sections, with the length of said tunnel housing sections being parallel to the centerline through said first and said second circular cuffs and said first and said second circular cuffs being made of a material with shape memory such that said first and said second circular cuff will remain at shape of memory or will expand in response to an outside force and after said outside force is removed will remain at a circumference of a predetermined size as a function of the shape memory material of which it is made, b. said one or more tunnel housing sections made of a material compatible with material of which said first and said second circular cuffs are made with length greater than depth and depth greater than width, and length parallel to the centerline of and equal to width of said first and said second cuffs, and depth extending beyond inside circumference of said first and said second circular cuffs, containing a first tunnel and second tunnel of the same cross-section, said first and said second tunnels being lined with material of which said one or more tunnel sections are made with said first tunnel having a flared entry port, on a longitudinal end of said tunnel housing section and coursing approximately straight along the length, for a distance greater than the length of a short suture to be placed in said first tunnel, then curving through the depth with curve being same as that of said short suture when unconfined to an out port on a plane at a right angle with respect to the plane of said entry port, and said second tunnel having a through port opening on the same side of said tunnel housing section as said out port, at a distance equal to diameter of and in location corresponding to original unconfined shape of said short suture as it emerges from said out port and said second tunnel coursing in same curved path to an end port in said second tunnel of said tunnel housing section and with said out port and said through port being on the outside circumference of said circular cuff, c. one or more short sutures of material having a shape memory being of the same cross-section, and slidably smaller than said first and said second tunnels, having a blunt proximal end and sharp distal end, with said short suture being biased in a curved circular shape during manufacture so said proximal and said distal ends are touching in same or adjacent planes to which said short suture will return after being released from any other shape forced on said short suture by being forced into said first tunnel, d. a graft tube having a proximal and a distal end where said first and said second circular cuffs are respectively attached, and circumferences on said proximal and distal ends and points fit against lumen walls when said graft tube is concentrically located in said lumen after entering the vascular system through a skin puncture, made of a flexible material with reinforcing rings that spiral tending to prevent said graft tube from changing said circumferences when stretched, and said graft tube being capable of being covered or lined with materials that encourage bioactive endothelial growth, e. a first and a second shroud, continuous with or attached to said first and said second circular cuff, but not blocking said entry ports, being of a material that is the same as or will bond with said graft tube but having no reinforcing rings, of slidably larger circumference than said graft tube to which said shroud is attached by a joint, f. a first and a second push rod support member mounted on a push rod catheter, and of a circumference such that a plurality of push rods mounted on said circumference of said push rod support members will be in line with said entry ports in said tunnel housings on said first and said second circular cuffs, but when said first and said second push rod support members are not so aligned said support members will pass through said first and said second circular cuffs, g. said plurality of push rods mounted on the circumference of said first and said second push rod support members extending away from said first and said second push rod support members a sufficient distance to enter said first tunnel and push said proximal blunt end of said short suture a sufficient distance for said distal sharp end of said short suture to enter said end port, with said plurality of push rods being equal in number and equally spaced to be in line with said entry ports when said first and said second push rod support members are so aligned, h. said push rod catheter of strong flexible material having said second support member mounted distal to said first support member with push rods pointed distally and said first of said support members mounted proximal to said second support member with push rods pointed proximally and there is also one of two keyways both in the form of a longitudinal dent, one being in said push rod catheter under said second push rod support member, and two keys, both being in the form of a longitudinal protrusion shaped to fit in said keyways, one being located on said push rod catheter just proximal to ends of said pushrods, i. an inside and an outside holding catheter, made of strong flexible material and each having a distal and proximal end with said distal end of said inside holding catheter having a second holding member attached and having one of said two keys attached just proximal to said second holding member, and said distal end of said outside holding catheter having a first holding member attached and having one of said two keyways being located under said first holding member, j. said first and said second holding members sized to correspond to the size of said first and said second circular cuff, thus having a circumference smaller than the inner diameter of said first and said second circular cuff, and having one or more grooves in said outside circumference, equal in number, equally spaced to, and slidably larger than said tunnel housing sections protruding into the inner diameter of said circular cuff, and said first holding member being concentrically mounted on said distal end of said outside holding catheter and said second holding member being concentrically mounted on said distal end of said inside holding catheter, and when moved to opposite side of said circular cuffs said keys and said keyways are moved a sufficient distance to disengage allowing rotation which engages said tunnel housing sections between said grooves to hold said tunnel housing sections against force from said push rods, k. a first expansion balloon mounted on said distal end of said inside catheter and a second expansion balloon mounted on said distal end of said outside catheter, being a means of delivery and a means of expanding said circular cuff, each having said one or more grooves in said outside circumference, equal in number, equally spaced to, and slidably larger than said tunnel housing sections protruding into the inner diameter of said first and said second circular cuff to which it is applied and having an uninflated circumference smaller than, a semi-inflated circumference equal to, and fully-inflated diameter larger than said inner diameter of said first and said second circular cuff, and thus capable of gripping, holding, and increasing the circumference of said first and said second circular cuff, and aligning said keys and said keyways on said outside and said inside holding catheters, whereby, said first and second expansion balloons when placed within said central openings of said first and said second circular cuff and inflated to grip said first and said second circular cuff enables operator to advance said inside and said outside catheter with said first and second expansion balloons on their distal ends causing said first and said second circular cuff to advance by pulling and pushing said shrouds, said graft tube and said first and said first and said second circular cuff through said vasculature until reaching a predetermined distal site where said second circular cuff is to be attached to said lumen wall, and where said first circular cuff is located at a preselected proximal site thus accomplishing delivery, whereupon said expandable balloons is inflated to a preselected size to make said first and said second circular cuff contiguous, then deflated and either removed from body and be replaced with an alternative holding member or remain and be used as said first and second holding member, such that said holding members and said push rod support members are advanced through said graft tube so that grooves in said holding members are thus aligned with said tunnel housing sections protruding into the inner diameter of said circular cuffs and said keys and said keyways are engaged thus causing said push rods to be aligned with said entry ports whereupon operator moves said holding members out of said circular cuffs to opposite side and rotates them to engage protruding tunnel housing sections, then operator by pulling and pushing said holding catheters and said push rod catheters with opposite and equal force will cause said push rods to enter said tunnels and cause each said short suture to move through said first tunnel, leave through said exit port, resume its original circular shape when no longer in said first tunnel, enter and curve through the adjacent lumen wall, and enter said second tunnel through said through port to continue through said second tunnel to said end port, thereby connecting said circular cuffs to said lumen wall whereupon said circular cuffs remain at any predetermined circumference depending on the materials used in manufacture graft tube, circular cuffs, sutures and shrouds are capable of being covered with a bioactive endothelial growth factor.

2. The device of claim 1 further including:

a delivery catheter of circumference slidably smaller than the lumen circumference of the segment of vasculature where said graft tube is preselected to be attached, and slidably larger than said graft tube, said circular cuffs, said shrouds and said bioactive endothelial growth factor, whereby said circular cuffs, said graft tube, said shrouds and said bioactive endothelial growth factor are protectively enclosed in said delivery catheter while operator simultaneously advances said delivery catheter and said expandable balloons to preselected intended site of emplacement, whereupon with said expandable balloons gripping said circular cuffs, said delivery catheter is withdrawn from said vessel, leaving said graft tube and said circular cuffs in the preselected location.

3. The device of claim 1 further including, a plurality of incisions made over the surface of said short sutures at an angle pointed toward said distal end of said short sutures, whereby the incisions produce barbs that protrude from the surface with their sharp edges pointed away from the distal end and thus engaging the surface of said first and second tunnels in which said short sutures slide and thus causing resistance to said short sutures movement in a proximal direction after being advanced in the distal direction.

4. The device of claim 1 wherein, said sharp distal end on said short suture, being of a truncated angular shape as with a sharp chisel edge, whereby force is exerted on the truncated surface by tissue that said sharp distal end is pushed through thus urging said short suture in the opposite direction which is desired when said exit port and said through port are in adjacent planes.

5. The device of claim 1 further including, said first and said second tunnel linings and said short suture being made with a slippery coating, whereby less force is required to push said short sutures through said first and said second tunnels.

6. The device of claim 1 wherein, said alternative holding members being a rigid holding disc made of a non-expandable material and sized to correspond to the size of said first and said second circular cuffs such that said holding members will pass through said circular cuffs when said grooves are aligned with said tunnel housings but when rotated outside said circular cuff are not so aligned, whereby operator aligns said grooves and said tunnel housings and advances said holding discs through said circular cuffs and rotates said holding discs on other side of said circular cuffs thus holding said circular cuffs in place against any counterforce from push rods being advanced in said tunnel housing sections of said circular cuffs.

7. The device of claim 1 further including, a. said graft tube, said first and said second circular cuffs, said shrouds, said short sutures, said tunnel housing sections, including said tunnel linings, being made of a biodegradable material, b. said endothelial growth factor being a tissue-engineered vessel, whereby the graft tube and all other device components left in the body biodegrade over a period of time so that the only remaining elements is a tissue-engineered vessel for which the bio-absorbed components provided a scaffold during the time the tissue engineered vessel grew into the non-diseased tissue of the lumen wall to constitute a new conduit for the flow of blood.

8. The device of claim 1 further including, a. an additional circular cuff located between said proximal end and said distal end of said graft tube and being of a circumference smaller than said first circular cuff and equal to circumference of said second circular cuff which is smaller than said first circular cuff to accommodate a graft tube with tapered distal end, b. said holding member, said holding catheter, said push rod member, said push rod catheter and said shroud being of a size and circumference to correspond to respective sizes of said additional circular cuff, said first circular cuff and said second circular cuff, whereby an especially long graft tube needed to extend from proximal end in upper thigh to distal end below knee in calf requires taper to match size of vessels in thigh and calf, is accommodated by having said holding member, said holding catheter, said push rod member, said push rod catheter and said shroud of a size to accommodate said first, said second and said additional circular cuffs so to place said circular sutures at each.

9. The device of claim 1 wherein, said shroud being of a circumference to form a butt joint with said graft tube, whereby a heat bonding device for making a butt joint can be used to make the butt joint.

10. The device of claim 1 wherein, whereby said expandable balloon as holding member is deflated to move through said inner diameters of said circular cuffs, semi-inflated with grooves aligned with tunnel housings when inside said inner diameters and rotated or fully inflated on opposite side of said first and said second circular cuffs thus holding said cuffs.

11. The device of claim 1 wherein, each said push rod support member being an expandable balloon mounted on said push rod catheter having circumference when fully inflated that aligns said plurality of push rods located around said circumference and pointed distally with said entry ports of said tunnel housing sections in said second circular cuffs and said push rods pointed proximally with said tunnel housings in said first circular cuff, and when less than fully inflated being of a circumference that will pass through said first and said second circular cuffs.

12. The device of claim 1 wherein, said plurality of support members are rigid support members extending from each one of said plurality of said push rods to either said first or said second push rod catheters being a distance and angle such that said push rods are in alignment with said exit ports when said push rod catheters are in said graft tube, whereby operator advances said rigid support members on said push rod catheters so said push rods, being aligned with said tunnel housings, enter said end ports of said first tunnels thus pushing said short sutures out of said first tunnel and into said second tunnel so as to attach said circular cuffs to said lumen wall with said short sutures.

13. The device of claim 1 wherein, said sharp point of said short suture is in the shape of a pencil point, whereby passage through tissue places pressure equally on all sides of point, thus not influencing direction of movement and thus tending to keep said sharp point in same plane as said blunt end of said short suture.

14. The device of claim 1 further including, an undulating wire in said first and said second circular cuff made of material that has a shape memory urging said wire to return to an original shape after being deformed to another shape by an outside force, whereby said first and said second circular cuffs are provided with a further means of expanding in response to an outside force exerted on the inside of said first and said second circular cuff and after outside force is removed returning to original shape as a function of the material and undulating shape of which it is made.

* * * * *